United States Patent [19]

Radocy et al.

[11] 4,225,983
[45] Oct. 7, 1980

[54] PROSTHETIC TERMINAL DEVICE

[76] Inventors: Robert Radocy, 2860 Pennsylvania Ave., Boulder, Colo. 80303; Ronald E. Dick, Magnolia Star Rte., Nederland, Colo. 80466

[21] Appl. No.: 957,338

[22] Filed: Nov. 2, 1978

[51] Int. Cl.³ .............................................. A61F 1/06
[52] U.S. Cl. ........................................... 3/12; 3/12.7
[58] Field of Search ................. 3/12, 12.6, 12.7, 12.8, 3/12.4, 12.5, 12.1

[56] References Cited

U.S. PATENT DOCUMENTS

| | | | |
|---|---|---|---|
| 1,284,875 | 11/1918 | Caron | 3/12.8 |
| 2,364,313 | 12/1944 | Pecorella | 3/12.7 |
| 2,415,145 | 2/1947 | Mollenhour | 3/12.8 X |
| 2,493,841 | 1/1950 | Threewit | 3/12.6 X |
| 2,631,295 | 3/1953 | Becker | 3/12 |

FOREIGN PATENT DOCUMENTS 283314  1/1928  United Kingdom .......................... 3/12

*Primary Examiner*—Ronald L. Frinks
*Attorney, Agent, or Firm*—Richard D. Law

[57] ABSTRACT

A voluntary closing prehensile prosthetic hand of laminated construction having a natural reaching and positive gripping action, innate biofeedback characteristics, and greater gripping strength and utility. The thumb member is a cable actuated, rotatable member, which is spring biased to return to the open position. An internal hook, three co-operating gripping surfaces, and two manual locking devices provide a variety of closed positions for holding different sized objects. The overall design, which imitates the action of the human forefingers and thumb, results in a refined gripping action while increasing reaching and grasping capabilities.

10 Claims, 6 Drawing Figures

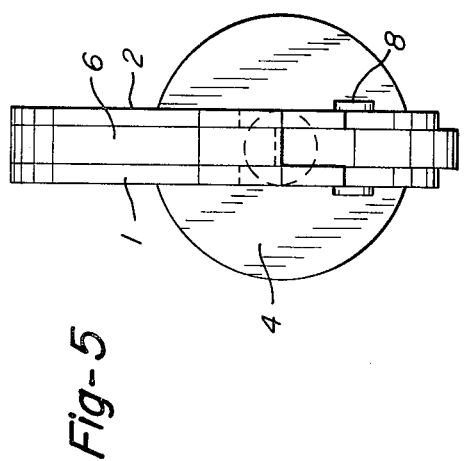
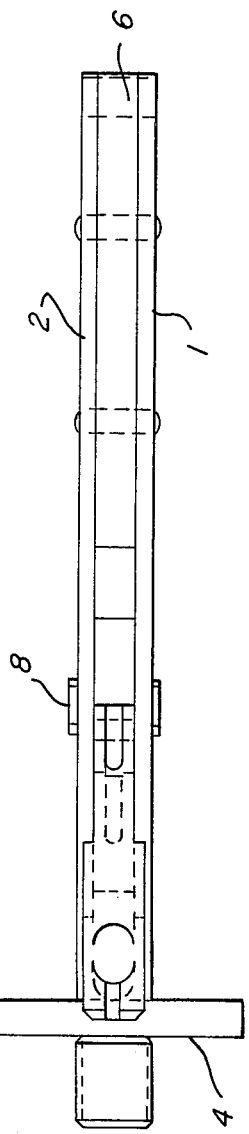

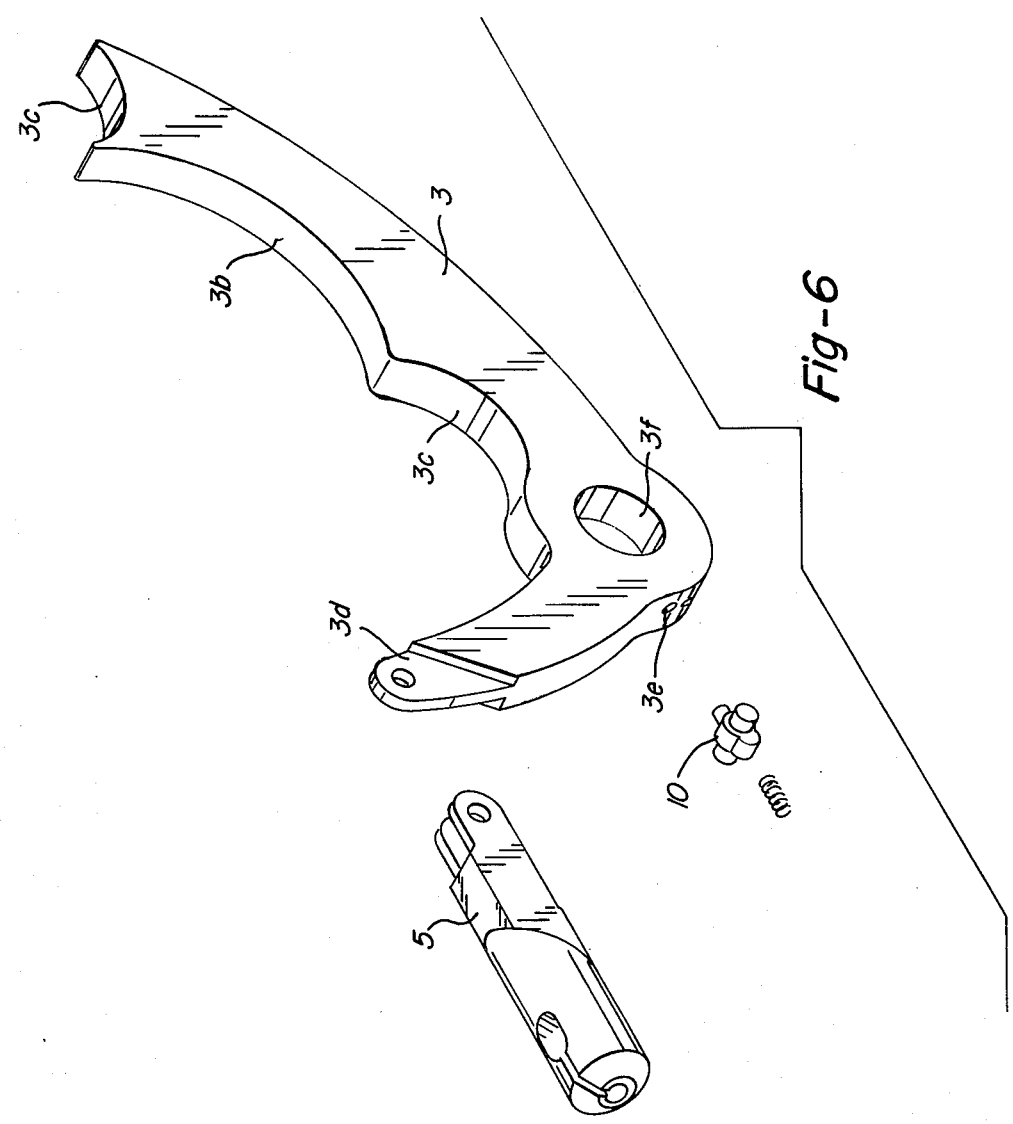

PROSTHETIC TERMINAL DEVICE

BRIEF SUMMMARY INCLUDING NATURE AND OBJECTS

The Voluntary Closing Prehensile Hand is a terminal device which relates to an improved and more economical construction.

An object of this invention is to provide an improved prosthetic hand with a natural reaching and positive gripping action with innate biofeedback characteristics by imitating or duplicating the action of the human forefingers and thumb.

Another objective of this invention is to provide an improved prosthetic hand with greater gripping strength and greater utility in grasping objects of various sizes and shapes without sacrificing manual dexterity or sensitivity.

Another objective of this invention is to provide an improved prosthetic hand of lower than "average" cost by utilizing a laminated construction of component materials which can be produced by less expensive "stamped" manufacturing processes, thus, eliminating the more expensive forged or casting processes.

Another objective of this invention is to provide an improved prosthetic hand with manual locking devices that function to lock the hand in a variety of closed positions.

Another objective of this invention is to provide an improved prosthetic hand which incorporates the reliable "hook" principle internally within the instrument thereby eliminating any puncturing tendencies of the hook.

Another objective of this invention is to provide an improved prosthetic hand which will readily adapt to existing prosthesis design, thus, allowing easy conversion both mechanically and physically, with minimum time required for functional re-education.

Another objective of this invention is to optimize cable movement thereby refining the gripping action and simultaneously increasing reaching and grasping capabilities.

DESCRIPTION OF VIEWS

These and other objects and advantages of the invention will be more fully apparent from the following description, given with the accompanying drawings, wherein like reference numerals refer to the same parts throughout the various views, and in which:

FIG. 4 is a top plan view of the index member.

FIG. 5 is an end view of FIG. 1.

FIG. 6 is an exploded isometric view of the thumb member, cable adapter, and primary lock.

DETAILED DESCRIPTION

Figure 1:
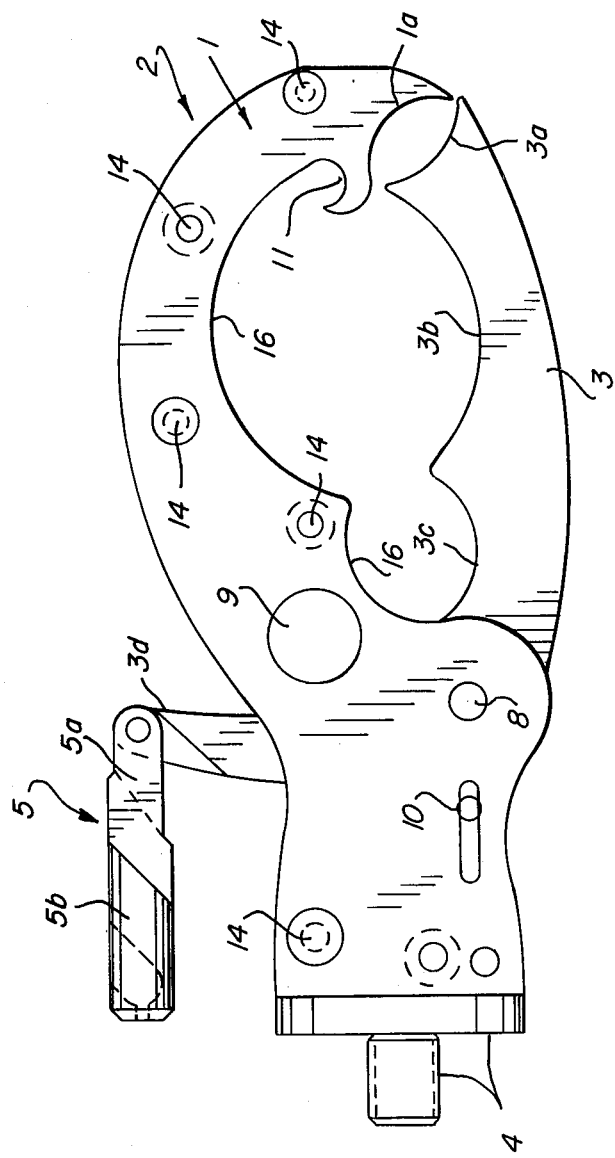
FIG. 1 is a side view, with the thumb member closed to the point of meeting the index member.

With continued reference to the figures, the invention comprises index member plates 1 and 2, thumb member 3, wrist adapter 4, cable adapter 5, index member re-inforcing plate 6, main spring 7, pivot axle 8, primary lock assembly 10, bearings 12, and threaded fasteners 14.

FIGS. 4 and 5, a top and end view, illustrates the laminated construction which sandwiches re-inforcing plate 6, and the framework which supports the pivot axle 8 of thumb member 3.

Figure 2:
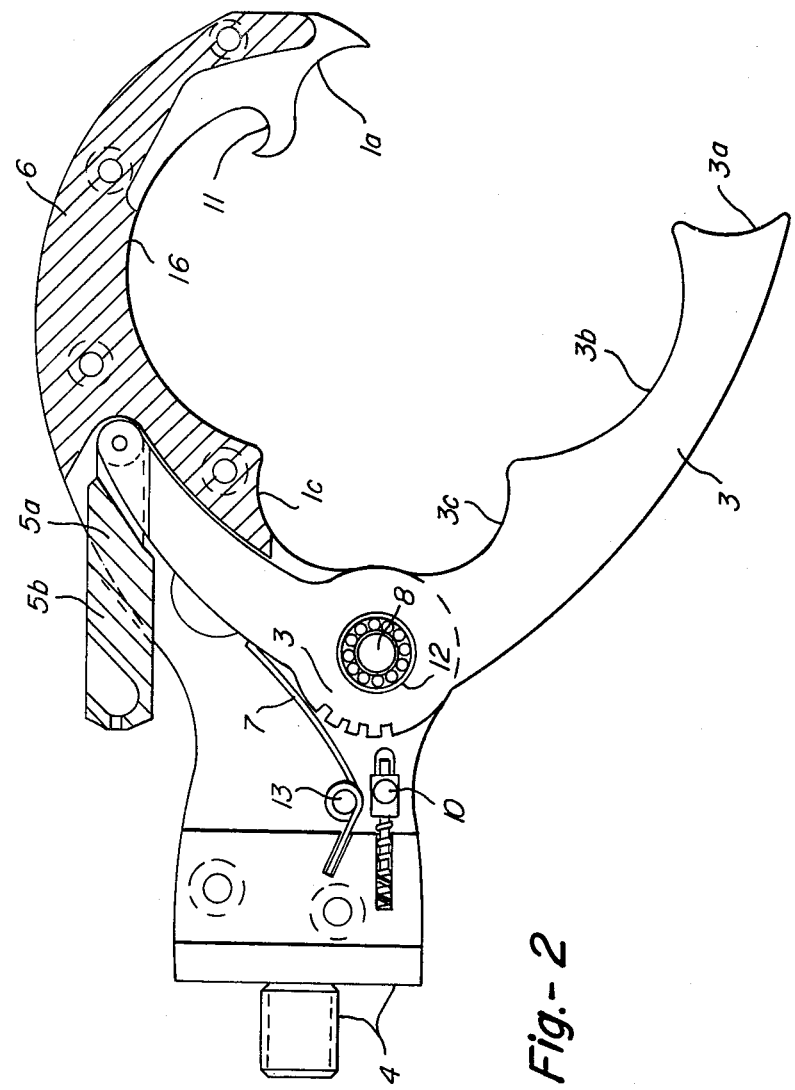
FIG. 2 is a side view, with the upper index member plate removed, and several internal components cut away to better illustrate their construction. The thumb member is positioned fully open in this view.

From a fully open position (FIG. 2) the thumb member 3 closes by voluntarily controlled cable tension through cable adapter 5 (comprised of components 5a and 5b in FIG. 1); rotating simultaneously around bearings 12 and pivot axle 8, thumb member surfaces 3a, 3b, and 3c co-operate with index member surfaces 1a, 1b, and 1c to provide three gripping potentials. Gripping surfaces 1a and 3a provide capabilities for precise and sensitive gripping action, while gripping surfaces 1b and 3b, and 1c and 3c provide capabilities for gripping larger objects.

The tip of thumb member 3 passes through a channel between index member plates 1 and 2 and is limited by the index member re-inforcing plate 6.

The configuration of the internal hook 11 provides for the advantages of a hook yet decreases the probability of an inadvertant puncture.

Figure 3:
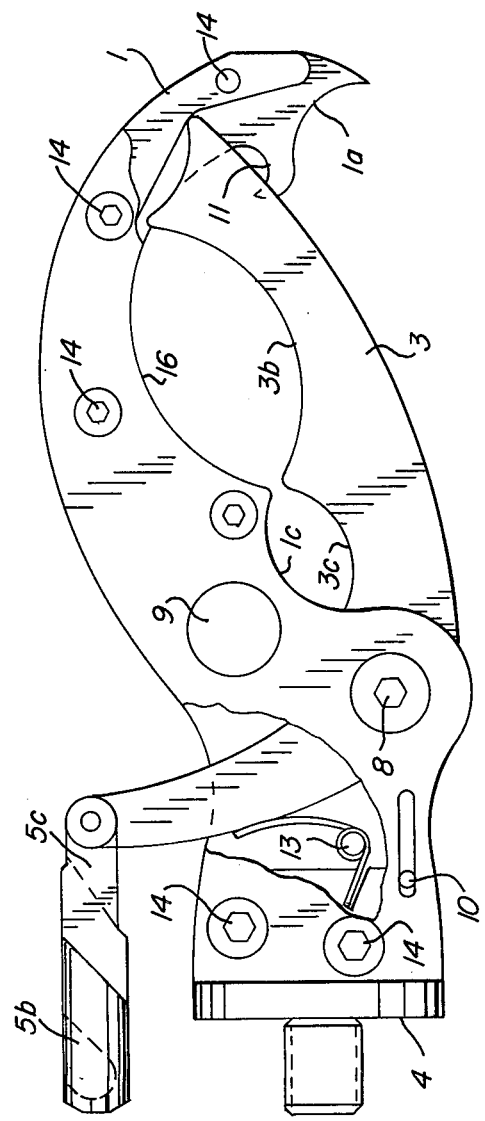
FIG. 3 is a side view, with the thumb member positioned fully closed. A partial cut-away illustrates inner construction and component positions with the thumb member closed.

The primary locking device (FIG. 5) is activated by pressing the release button on lock 10, which releases the bias spring to force the forwardly extending pin through annulated channel (FIG. 3) within index member plates 1 and 2, into one of the locking receptacles 3e in thumb member 3.

Spring 7 (FIG. 2) mounted within slot in wrist adapter 4, biases voluntary closing force for optimum return reflex action, around pin 13.

A secondary locking device (FIG. 1) provides a single position locking opportunity by insertion of a foreign body into hole 9 thereby blocking the return of thumb member 3.

It has been found that there is an optimal functional relationship of the proportions of the component parts to produce optimal movement. These distances are about 2.5 inches between the tip of the index and thumb members; a pivot axle point about 0.5 inches below and parallel to the center line of the terminal device; angle of about 94 degrees between segments of the thumb member; and a cable movement of about 2.25 inches.

While we have shown and described a preferred embodiment of the invention, it will be apparent to those skilled in the art to which it relates that the invention is capable of variations and modifications from the form shown so that the scope thereof should be limited by the proper scope of the claims appended hereto.

What we claim is:

1. A prosthetic, voluntary closing hand comprised of a wrist adaptor an index member extending therefrom, a thumb member pivoted to the index member, a bias spring engaging said thumb member to urge the thumb member to open position with respect to said index member, and a cable to urge said thumb member towards said index finger in closing position for hand grasping functions,
   (A) said index member having a movable thumb locking device mounted thereon, and a first inner surface defining three cooperating gripping surfaces extending along its length,
   (B) said thumb member having a plurality of locking receptacles for receiving said movable thumb locking device to selectively lock said thumb in a plurality of angular positions with respect to said index member, and a second inner surface facing said first inner surface defining three cooperating gripping surfaces along its length for cooperation with the index member gripping surfaces to grasp objects of different size and;

(C) said wrist adapter incorporating a standard threaded bolt for attachment to wrist units found on standard arm prosthesis.

2. A prosthetic hand as defined in claim 1, wherein said index member is provided with an internal hook along said first internal surface.

3. A prosthetic hand as defined in claim 2, wherein said internal hook is positioned between two of said cooperative gripping surfaces.

4. A prosthetic hand as defined in claim 1, wherein said three cooperating surfaces extend from the tip of said thumb member and said index member, and said cooperating surfaces at the tips of said index member and said thumb member are small concave surfaces positioned for cooperating toward a closed position for gripping small objects therebetween.

5. A prosthetic hand as defined in claim 4, wherein said thumb member and said index member are arcuate forming a pair of larger cooperating surfaces adjacent said pair of cooperating small concave surfaces at the tips of said index member and said thumb member.

6. A prosthetic hand as defined in claim 5, wherein an internal hook is positioned between said larger cooperating surface and said small concave surface at the tip of said index member.

7. A prosthetic hand as defined in claim 1, wherein said index member is a reinforced laminate of a reinforcing plate and index member plates on either side thereof.

8. A prosthetic hand as defined in claim 7, wherein said index member plates extend beyond said reinforcing plate, and said thumb member tip passes between said index plates and is limited for further movement by said reinforcing plate.

9. A prosthetic hand as defined in claim 1, wherein said wrist adapter has means housing a biasing spring that engages said movable thumb locking device.

10. A prosthetic hand as defined in claim 1, wherein said thumb member has two segments defining an angular bend therebetween and pivot axle extends through said bend to pivot said thumb member to said index member and the optimal functional relationship proportioned among the component parts are around, (A) cable movement about 2.25 inches,
(B) opening distance between the tip of the index and thumb members about 2.5 inches,
(C) angle of bend between segments of thumb member about 94 degrees, and
(D) pivot axle point about 0.5 inches below and parallel to the center line of the prosthetic hand.

* * * * *